United States Patent
Cook et al.

(10) Patent No.: US 8,968,413 B2
(45) Date of Patent: Mar. 3, 2015

(54) ORTHOPAEDIC TIBIAL PROSTHESIS HAVING TIBIAL AUGMENTS

(71) Applicants: Michael A. Cook, Claypool, IN (US); Stephanie M. Wainscott, Warsaw, IN (US); Tyler S. Hathaway, Auburn, IN (US); Joseph G. Wyss, Fort Wayne, IN (US)

(72) Inventors: Michael A. Cook, Claypool, IN (US); Stephanie M. Wainscott, Warsaw, IN (US); Tyler S. Hathaway, Auburn, IN (US); Joseph G. Wyss, Fort Wayne, IN (US)

(73) Assignee: DePuy (Ireland) (IE)

(*) Notice: Subject to any disclaimer, the term of this patent is extended or adjusted under 35 U.S.C. 154(b) by 7 days.

(21) Appl. No.: 13/828,937

(22) Filed: Mar. 14, 2013

(65) Prior Publication Data

US 2014/0277539 A1     Sep. 18, 2014

(51) Int. Cl.
*A61F 2/38* (2006.01)
*A61F 2/30* (2006.01)

(52) U.S. Cl.
CPC . *A61F 2/389* (2013.01); *A61F 2/30* (2013.01); *A61F 2/30734* (2013.01); *A61F 2/38* (2013.01); *A61F 2002/30133* (2013.01); *A61F 2002/3021* (2013.01); *A61F 2002/30214* (2013.01)
USPC ..................... 623/20.32; 623/20.33

(58) Field of Classification Search
CPC ...................... A61F 2/389; A61F 2002/30878
USPC ........................... 623/20.32–20.34
See application file for complete search history.

(56) References Cited

U.S. PATENT DOCUMENTS

2004/0049284 A1* 3/2004 German et al. ............ 623/20.15
2004/0162619 A1* 8/2004 Blaylock et al. ........... 623/20.16

* cited by examiner

*Primary Examiner* — Jason-Dennis Stewart
(74) *Attorney, Agent, or Firm* — Barnes & Thornburg LLP

(57) ABSTRACT

A tibial orthopaedic prosthesis assembly for use during performance of a knee replacement procedure includes one or more tibial augments configured to be coupled to a tibial tray. Each tibial augment includes an exterior side surface of varying angulation relative to a top surface of the tibial augment.

18 Claims, 8 Drawing Sheets

ORTHOPAEDIC TIBIAL PROSTHESIS HAVING TIBIAL AUGMENTS

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. A typical knee prosthesis includes a tibial component, a femoral component, and an insert or bearing component positioned between the tibial component and the femoral component. In the case of a knee replacement procedure, a tibial tray is implanted into the patient's tibia. A bearing is secured to the tibial tray. The condyle surfaces of a replacement femoral component bear against the tibial bearing.

A typical tibial tray includes a platform or plate having a stem post extending distally therefrom. The stem post of the tibial tray is configured to be received in a surgically-prepared medullary canal of the patient's tibia, and may include stem component or broach attached thereto. Depending on the amount of bone loss or deterioration, tibial augments may be used with the tibial tray to increase the overall volume of the tibial tray and compensate for the loss of bone in particular areas. Additionally, such tibial augments may improve the fixation of the tibial tray to the patient's tibia by reducing the amount of bone cement or other adhesive required to secure the tibial tray to the patient's tibia.

SUMMARY

According to one aspect, a tibial augment configured to be secured to an implantable prosthetic tibial tray may include a top proximal surface that abuts a bottom surface of the tibial tray when the tibial augment is secured to the tibial tray. The tibial augment may also include a bottom distal surface opposite the top proximal surface. The tibial augment may also include an exterior side surface that extends from the top proximal surface to the bottom distal surface. The exterior side surface may include a side surface section extending from an anterior-most point of the exterior side surface to a posterior-most point of the exterior surface. The side surface section may define a first interior angle relative to the top proximal surface at the anterior-most point of the exterior side surface and a second interior angle relative to the top proximal surface at the posterior-most point of the exterior side surface that is different from the first interior angle.

In some embodiments, the second interior angle is less than the first interior angle. Additionally, in some embodiments, the second interior angle may be an acute angle. Further, in some embodiments, the first interior angle may be a right angle.

In some embodiments, the side surface section may define a right angle relative to the top proximal surface at the anterior-most point of the exterior side surface and an acute interior angle relative to the top proximal surface at the posterior-most point of the exterior side surface.

In some embodiments, the side surface section may define a third interior angle relative to the bottom distal surface at the anterior-most point of the exterior side surface, the third interior angle being substantially equal to the first interior angle.

In some embodiments, the side surface section may define a third interior angle relative to the bottom distal surface at the posterior-most point of the exterior side surface, wherein the third interior angle is an obtuse angle.

Additionally, in some embodiments, the side surface section may have a non-constant angulation relative to the top proximal surface as the side surface section extends from the anterior-most point of the exterior side surface to the posterior-most point of the exterior side surface.

In some embodiments, the side surface section may define a third interior angle relative to the top proximal surface at a mid-point between the anterior-most point and the posterior-most point of the exterior side surface, wherein the third interior angle is an acute angle.

The third interior angle may be different from each of the first interior angle and the second interior angle. Additionally, in some embodiments, the top proximal surface may have a surface area that is substantially greater than a surface area of the bottom distal surface.

Additionally, in some embodiments, the tibial augment may include a medial end surface extending from the top proximal surface to the bottom distal surface and from the exterior side surface to an interior side surface of the tibial augment, and the medial end surface may have a constant width. The width of the medial end surface may be at least 3 millimeters.

In some embodiments, the tibial augment may have an interior surface defining a mounting aperture that extends through the tibial augment and has a first opening defined in the top proximal surface and a second opening defined in the bottom distal surface. Additionally, in some embodiments, the bottom distal surface may include a recess defined therein to receive a bracket of the tibial tray when the tibial augment is secured to the tibial tray.

According to another aspect, an implantable orthopedic knee prosthesis may include a tibial tray, a medial tibial augment secured to a medial side of the bottom surface of the platform, and a lateral tibial augment secured to a lateral side of the bottom surface of the platform. The tibial tray may include a platform and a stem extending downwardly from a bottom surface of the platform, the platform including a top surface, opposite the bottom surface, to receive a tibial bearing. The medial tibial augment may include a first top surface that abuts the bottom surface of the platform, a first bottom surface opposite the first top surface, a first exterior side surface extending from the first top surface to the first bottom surface, a first interior side surface extending from the first top surface to the first bottom surface, and a first medial end surface extending from the first top surface to the first bottom surface and from the first exterior side surface to the first interior side surface of the tibial augment. The first medial end surface may have a constant width. The lateral tibial augment may include a second top surface that abuts the bottom surface of the platform, a second bottom surface opposite the second top surface, a second exterior side surface extending from the second top surface to the second bottom surface, a second interior side surface extending from the second top surface to the second bottom surface, and a second medial end surface extending from the second top surface to the second bottom surface and from the second exterior side surface to the second interior side surface of the tibial augment. The second medial end surface may have a constant width. Additionally, the first medial end surface and the second medial end surface may oppose each other toward an anterior side of the platform and are may be spaced apart from each other.

In some embodiments, the first medial end surface and the second medial end surface are spaced apart by at least 2 millimeters. For example, in some embodiments, the first medial end surface and the second medial end surface are spaced apart by at least 5 millimeters.

Additionally, in some embodiments, the first top surface of the medial tibial augment may have a surface area that is greater than the surface area of the first bottom surface of the medial tibial augment, and the second top surface of the lateral tibial augment may have a surface area that is greater than the surface area of the second bottom surface of the lateral tibial augment.

According to another aspect, a tibial augment configured to be secured to an implantable prosthetic tibial tray may include a top proximal surface that abuts a bottom surface of the tibial tray when the tibial augment is secured to the tibial tray prosthesis, a bottom distal surface opposite the top proximal surface, and an interior surface defining a mounting aperture that extends through the tibial augment and has a first opening defined in the top proximal surface and a second opening defined in the bottom distal surface. The top proximal surface may have a surface area substantially greater than the surface area of the bottom distal surface.

BRIEF DESCRIPTION OF THE DRAWINGS

The detailed description particularly refers to the following figures, in which.

DETAILED DESCRIPTION OF THE DRAWINGS

Figure 1:
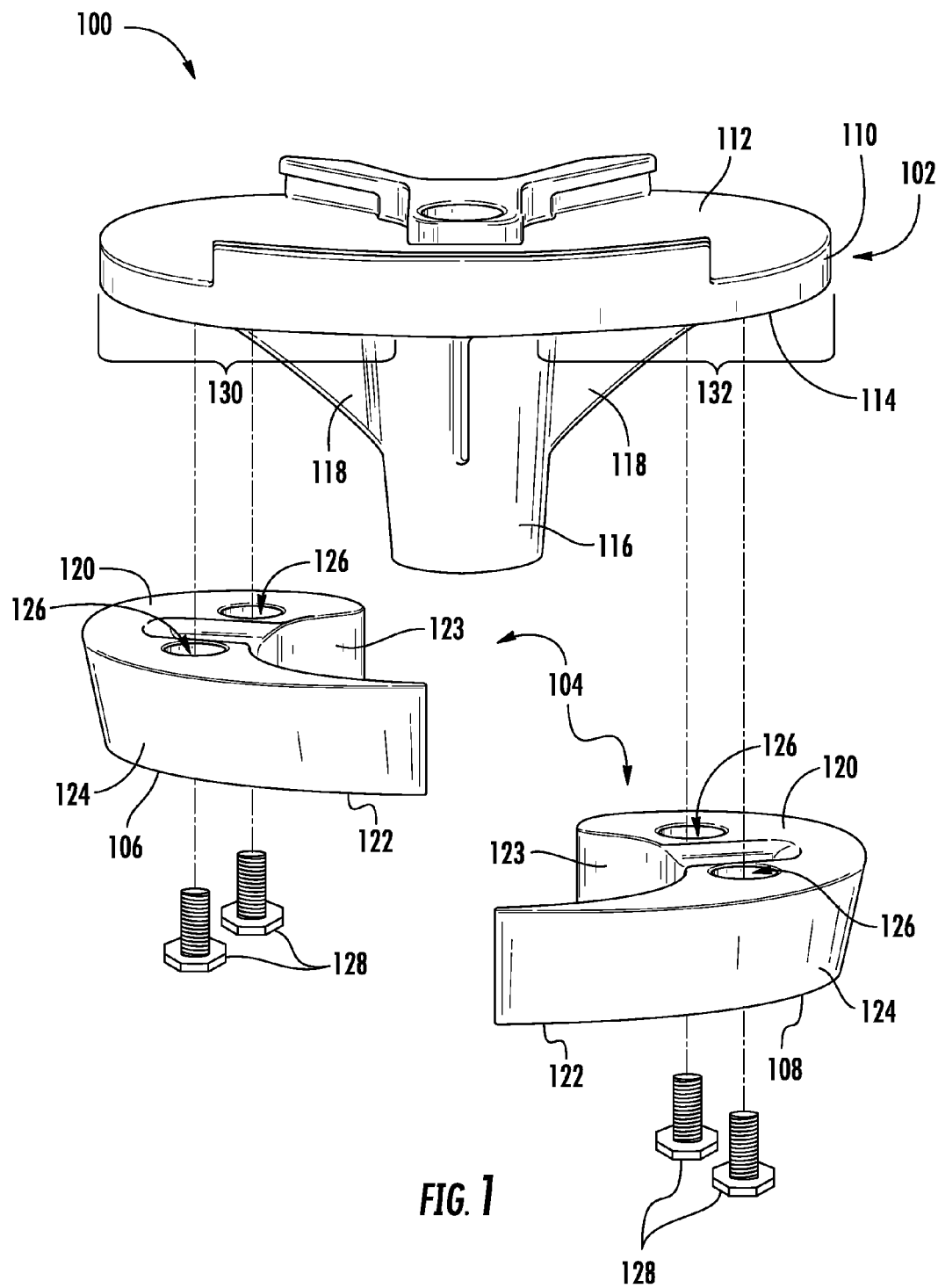
FIG. 1 is a perspective view of a tibial orthopaedic prosthesis assembly including a tibial tray and a pair of tibial augments.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, an illustrative tibial orthopaedic prosthesis assembly 100 includes a tibial tray 102 and one or more tibial augments 104. For example, in the illustrative embodiment, the tibial orthopaedic prosthesis assembly 100 includes a lateral tibial augment 106 and a medial tibial augment 108. The preceding designations of the tibial augments 104 as "lateral" and "medial" assume that the tibial orthopaedic prosthesis assembly 100 of FIG. 1 is implanted into, or otherwise configured for implantation into, the right knee of a patient. Of course, if the tibial orthopaedic prosthesis assembly 100 were implanted into the left knee of a patient, such designations would be reversed. As such, although the tibial augments 104 may be referenced below as "lateral" and/or "medial" tibial augments, it should be appreciated that such designations may be switched depending on the particular orthopedic procedure to be performed.

The tibial tray 102 is configured to be implanted into a surgically-prepared end of a patient's proximal tibia (not shown). The tibial tray 102 includes a platform 110 having a top surface 112 and a bottom surface 114. The bottom surface 114 includes a lateral side 130 and a medial side 132. Again, the "lateral" and "medial" designations of the tibial tray 102 assume that the tibial orthopaedic prosthesis assembly 100 of FIG. 1 is implanted into, or otherwise configured for implantation into, the right knee of a patient. However, such designations may be switched depending on the particular orthopaedic procedure to be performed (e.g., if the tibial tray 102 is to be implanted into the patient's left knee).

The tibial tray 102 further includes an elongated stem post 116 extending inferiorly away from the bottom surface 114 of the platform 110, and a pair of support brackets 118 secured to the bottom surface 114 of the platform 110 and to the stem post 116. The support brackets 118 serve to rigidly affix and support the stem post 116 to the platform 110. Although the illustrative tibial tray 102 includes two support brackets 118, the tibial tray 102 may include additional support brackets in other embodiments. Additionally, in the illustrative embodiment, the platform 110, stem post 116, and support brackets 118 are integral with each other and form a monolithic structure. However, in other embodiments, the stem post 116 and/or support brackets 118 may be separate from the platform 110 but secured thereto.

In use, a tibial bearing (not shown) may be coupled to the top surface 112 of the platform 110 of the tibial tray 102. The tibial bearing articulates with the natural or surgically-prepared distal end of a patient's femur (not shown).

Each of the tibial augments 104 includes a top proximal surface 120, a bottom distal surface 122, an interior side surface 123, and an exterior side surface 124. The top proximal surface 120 is configured to abut the bottom surface 114 of the tibial tray 102 when the tibial augment 104 is secured thereto. More specifically, the top proximal surface 120 of the lateral tibial augment 106 is configured to abut the lateral side 130 of the bottom surface 114, and the top proximal surface 120 of the medial tibial augment 108 is configured to abut the medial side 132 of the bottom surface 114. In the illustrative embodiment described herein, the bottom distal surface 122 of each tibial augment 104 is parallel to the top proximal surface 120.

Each of the tibial augments 104 also has defined therethrough one or more threaded mounting apertures 126. Each mounting aperture 126 extends through the corresponding tibial augment 104 and has openings defined in the top proximal surface 120 and in the bottom distal surface 122 of the corresponding tibial augment 104. Illustratively, each mounting aperture 126 is threaded and configured to receive a corresponding securing device 128, such as a screw or the like. In the illustrative embodiment, each tibial augment 104 includes two threaded mounting apertures 126 in each tibial augment 104. However, in other embodiments, each tibial augment 104 may include additional or fewer mounting apertures 126. Additionally, in other embodiments, the mounting apertures 126 may be non-threaded.

Figure 2:
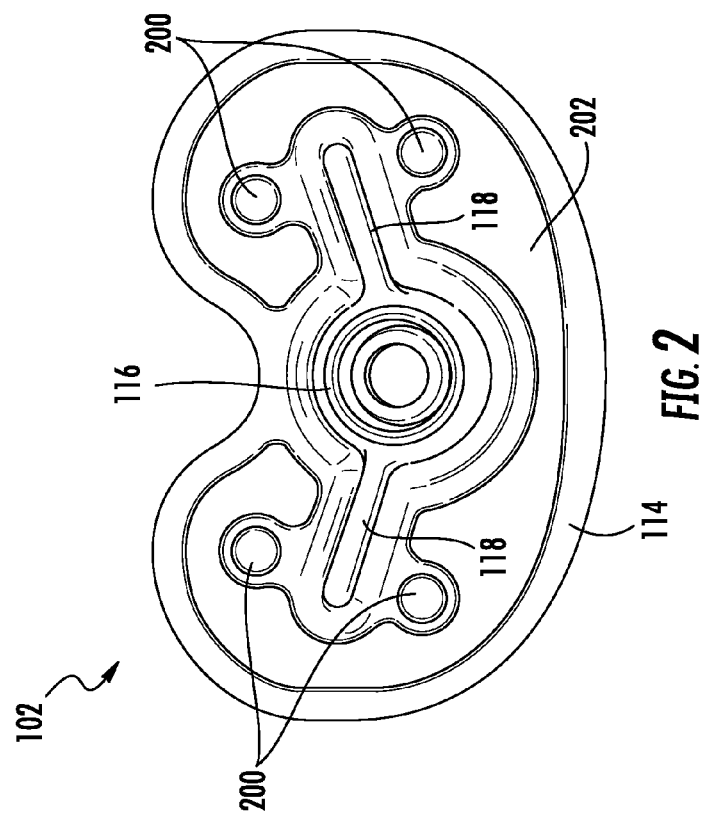
FIG. 2 is a bottom elevation view of a tibial tray of the tibial orthopaedic prosthesis assembly of FIG. 1.

The tibial augments 104 are attachable to the tibial tray 102 by inserting and fastening the securing devices 128 through the threaded mounting apertures 126 of the tibial augments 104 and into corresponding threaded bores 200 of the tibial tray 102, as depicted in FIGS. 1 and 2 and described in further detail below. In other embodiments, the tibial augments 104 may be secured to the tibial tray 102 by other or additional structures and/or mechanisms.

It should be appreciated that use of one or more tibial augments 104 may improve the fixation of the tibial orthopaedic prosthesis assembly 100 to a tibia of a patient. For example, during some knee replacement procedures, it may be found that the bony anatomy of the patient's tibia has undergone significant deterioration. As a result of such deterioration, attachment of a prosthesis to the patient's tibia may be difficult due to such bone loss, and bone ingrowth and fixation to the prosthesis may not occur as desired. The tibial augments 104 help to alleviate such difficulties by increasing the size of the tibial tray 102 to accommodate for such bone loss. Additionally, because the augmented tibial tray 102 fills up a greater volume of the patient's bony anatomy, less bone cement may be required for the particular orthopaedic surgical procedure to fill up voids caused by such bone loss.

The tibial tray 102 and the tibial augments 104 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. The tibial tray 102 and the tibial augments 104 may also be constructed with a polymeric material. One such polymeric material is polyethylene such as ultrahigh molecular weight polyethylene (UHMWPE). Additionally, the tibial tray 102 and the tibial augments 104 may be coated with a surface treatment, such as hydroxyapatite, to enhance biocompatibility. Moreover, the surfaces of the tibial tray 102 and the tibial augments 104 that engage the natural bone may be textured to facilitate securing those surfaces to the patient's bone. Such surfaces may also be porous coated to promote bone ingrowth for permanent fixation.

Figure 3:
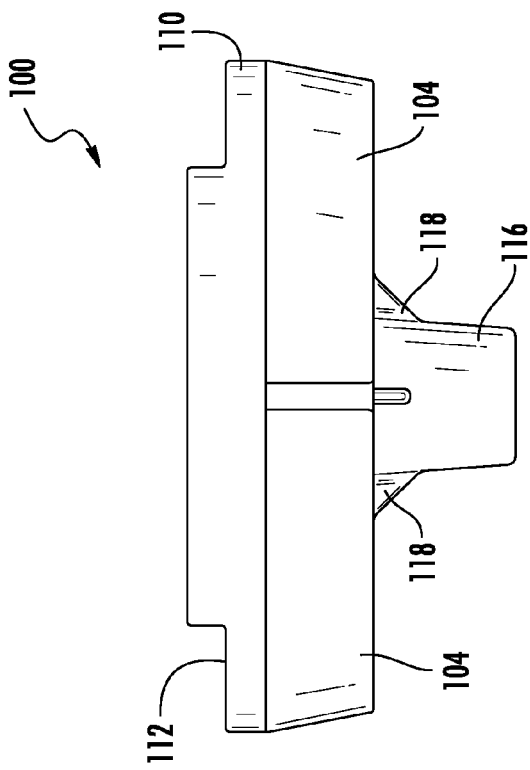
FIG. 3 is a front elevation view of the tibial orthopaedic prosthesis assembly of FIG. 1 with the tibial augments secured to the tibial tray.

As illustrated in FIG. 2, the bottom surface 114 of the platform 110 of the tibial tray 102 includes a plurality of threaded blind bores 200. The threaded blind bores 200 are configured to receive the securing devices 128 used to attach the tibial augments 104 to the tibial tray 102 as described above. In the illustrative embodiment described herein, the bottom surface 114 also includes a cement pocket 202, which may be filled with cement to further secure the tibial augments 104 to the bottom surface 114 of the tibial tray 102. In other embodiments, the bottom surface 114 may include various other types of cavities or pockets, which may be filled with other adhesive substances such as a glue appropriate for binding the tibial augments 104 to the tibial tray 102. The orthopaedic prosthesis assembly 100 having a pair of tibial augments 104 secured thereto is shown in FIG. 3.

Figure 5:
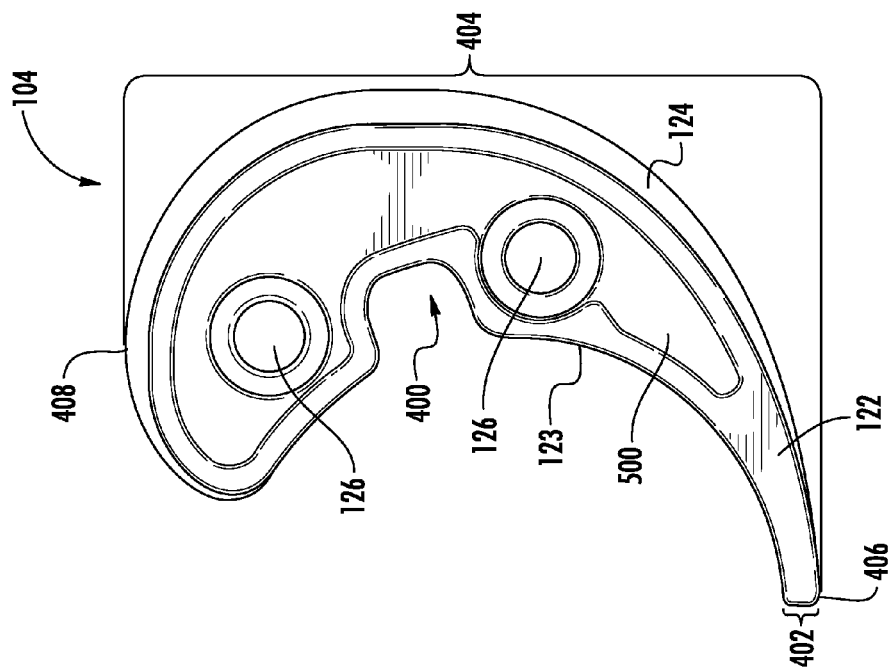
FIG. 5 is a bottom elevation view of the tibial augment of FIG. 4.
Figure 4:
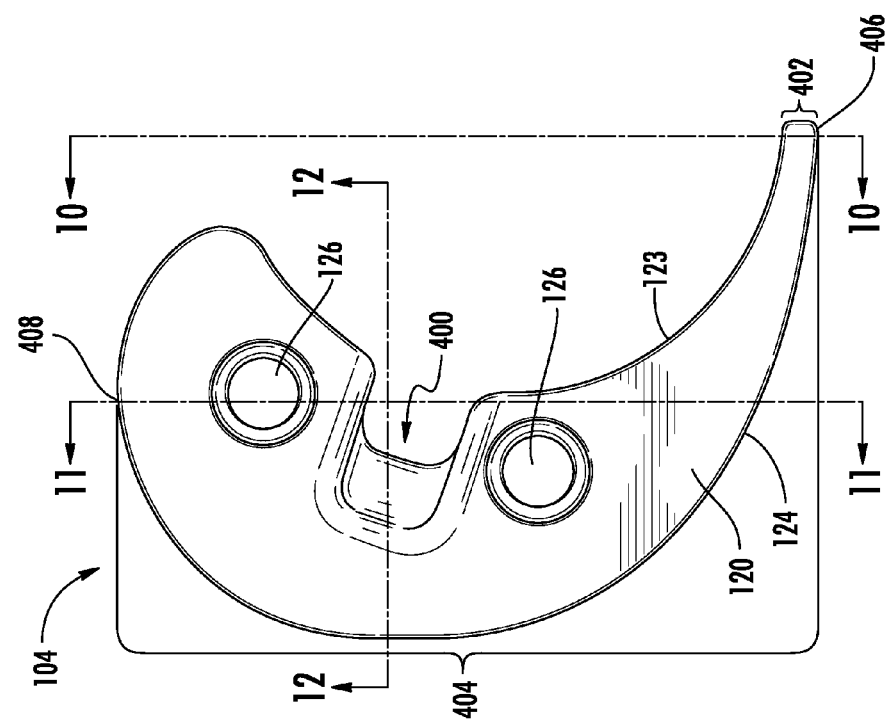
FIG. 4 is a top elevation view of a tibial augment of the tibial orthopaedic prosthesis assembly of FIG. 1.
Figure 12:
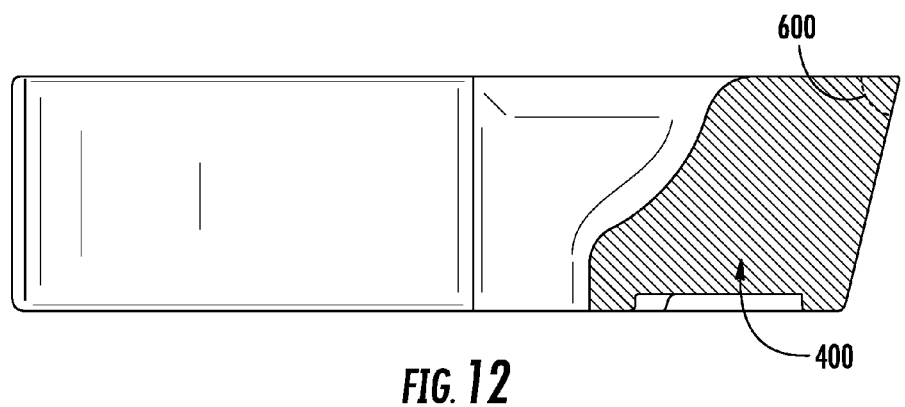
FIG. 12 is a cross section view taken along the line 12-12 of FIG. 4, as viewed in the direction of the reference arrows.

Referring now to FIGS. 4 and 5, each tibial augment 104 of the illustrative embodiment described herein also includes a recess 400 defined in the top proximal surface 120 thereof. As shown in FIG. 5, the recess 400 may extend through the tibial augment 104 and have an opening defined in the bottom surface 122 of the tibial augment 104. The recess 400, which is also depicted in cross-section in FIG. 12, is sized and shaped to receive a corresponding one of the brackets 118 of the tibial tray 102 in such a way as to allow the top proximal surface 120 of the corresponding tibial augment 104 to lie substantially flush against the bottom surface 114 of the platform 110 of the tibial tray 102.

Additionally, as shown in FIG. 5, the bottom distal surface 122 of each tibial augment 104 includes a cement pocket 500. In use, the cement pocket 500 may be filled with cement to aid in securing the tibial orthopaedic prosthesis assembly 100 to the tibia of a patient. Of course, in other embodiments, the bottom distal surface 122 of the tibial augment 104 may include various other types of cavities or pockets, which may be filled with other adhesive substances such as a glue appropriate for binding the tibial augments 104 to the patient's tibia.

Figure 6:
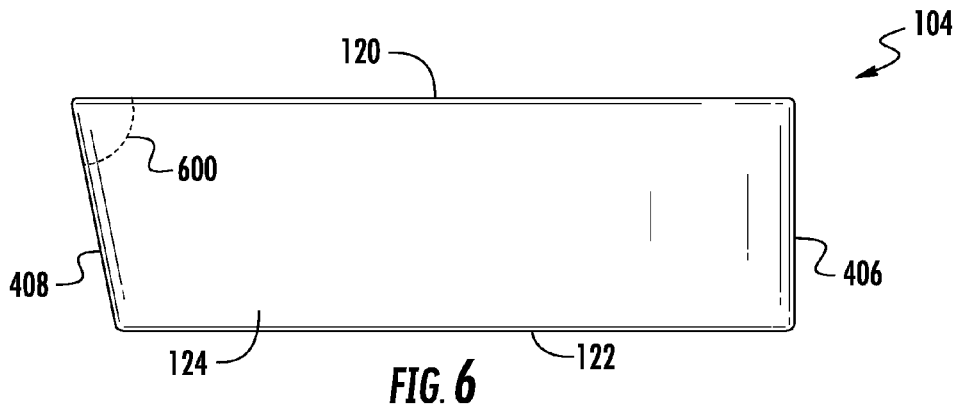
FIG. 6 is an anterior elevation view of the tibial augment of FIG. 4.
Figure 7:
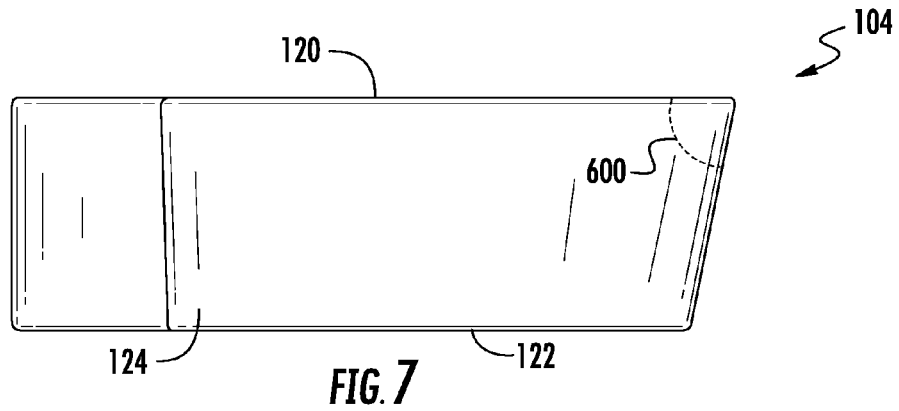
FIG. 7 is a posterior elevation view of the tibial augment of FIG. 4.
Figure 8:
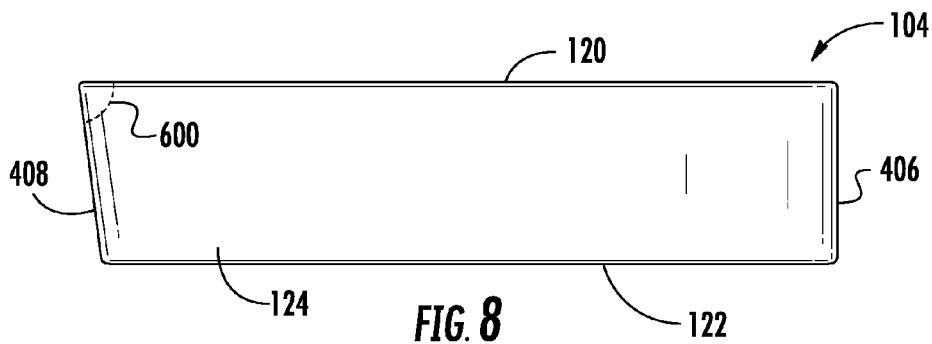
FIG. 8 is an exterior side elevation view of the tibial augment of FIG. 4.
Figure 10:
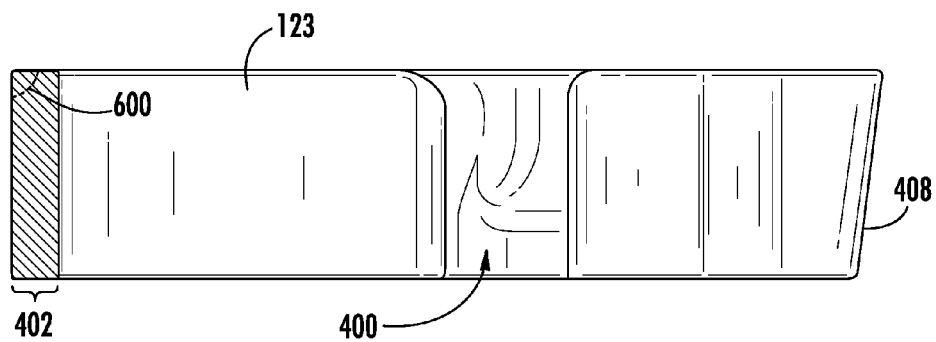
FIG. 10 is a cross section view taken along the line 10-10 of FIG. 4, as viewed in the direction of the reference arrows.
Figure 11:
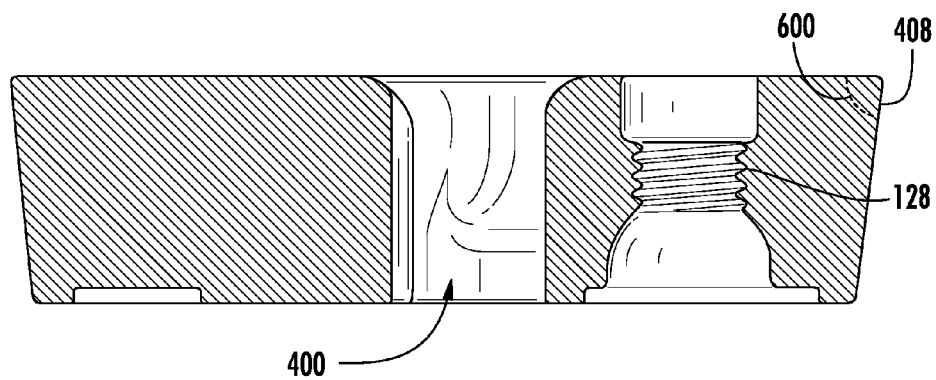
FIG. 11 is a cross section view taken along the line 11-11 of FIG. 4, as viewed in the direction of the reference arrows.

As discussed above, each tibial augment includes an exterior side surface 124. As shown in FIG. 4, the exterior side surface 124 includes a side surface section 404 extending from an anterior-most point 406 of the exterior side surface 124 to a posterior-most point 408 of the exterior surface 124. As best shown in FIGS. 6-8, the side surface section 404 defines an interior angle 600 relative to the top proximal surface 120 of the tibial augment 104 at each point along the exterior side surface 124. In the illustrative embodiment described herein, the interior angle 600 varies at the different points along the exterior side surface 124. For example, in the illustrative embodiment, the interior angle 600 defined by the side surface section 404 and the top proximal surface 120 at the anterior-most point 406 of the exterior side surface 124 (see, e.g., FIGS. 9 and 10) is greater than the interior angle 600 defined by the side surface section 404 and the top proximal surface 120 at the posterior-most point 408 of the exterior side surface 124 (see, e.g., FIGS. 6 and 11).

In the illustrative embodiment described herein, a 90° right angle is defined by the side surface section 404 and the top proximal surface 120 at the anterior-most point 406 of the exterior side surface 124. Because the bottom distal surface 122 of the tibial augment 104 is parallel to the top proximal surface 120 in the illustrative embodiment, the side surface section 404 and the bottom distal surface 122 also forms 90° right angle at the anterior-most point 406 of the exterior side surface 124. For example, in the illustrative embodiment described herein, the side surface section 404 extends orthogonally from (i.e., is perpendicular to) the top proximal surface 120 and/or the bottom distal surface 122 of the tibial augment at the anterior-most point 406 of the exterior side surface 124.

As further shown in FIGS. 6-8, as well as in FIGS. 3, 5, 9, and 15-17, the side surface section 404 may define angles relative to the top proximal surface 120 that are less than 90°

Figure 9:
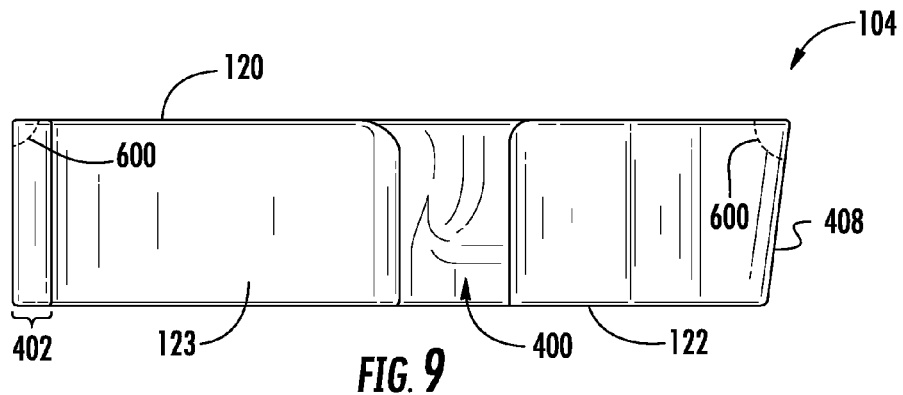
FIG. 9 is an interior side elevation view of the tibial augment of FIG. 4.

(i.e., form acute angles) at regions of the exterior side surface 124 other than at its anterior-most point 406. In particular and as illustrated in FIGS. 8 and 9, as well as in FIGS. 5 and 15-17, at its posterior-most point 408, the side surface section 404 defines an acute angle relative to the top proximal surface 120 of the tibial augment 104. Because the bottom distal surface 122 is parallel to the top proximal surface 120 in the illustrative embodiment described herein, the side surface section 404 also defines an angle greater than 90° (i.e., an obtuse angle) with the bottom distal surface 122.

As depicted in the above-noted figures, varying degrees of acute angles are formed by the side surface section 404 and the top proximal surface 120 at various points along the exterior side surface 124 between its posterior-most point 408 and its anterior-most point 406 in the illustrative embodiment described herein. In other words, the side surface section 404 has a non-constant angulation relative to the top proximal surface 120 as the side surface section 404 extends from the anterior-most point 406 to the posterior-most point 408 of the exterior side surface 124. In the illustrative embodiment described herein, the interior angle 600 formed by the side surface section 404 and the top proximal surface 120 gradually approaches 90° as the side surface section 404 extends near to the anterior-most point 406 of the exterior side surface 124. Because acute angles are defined by the side surface section 404 and the top proximal surface 120 as described above, the total surface area of the top proximal surface 120 is greater than that of the bottom distal surface 122. Of course, in other embodiments, the exterior side surface 124 may define an obtuse angle with the top proximal surface 120 at one or more points along the exterior side surface 124.

Referring back to FIGS. 4 and 5, each tibial augment 104 also includes a medial end surface 402. The medial end surface 402 resides at the anterior end of the tibial augment 104 and extends from the top proximal surface 120 to the bottom distal surface 122 and from the exterior side surface 124 to the interior side surface 123 of the tibial augment. In the illustrative embodiment described herein, the medial end surface 402 has a constant width as it extends from its proximal end to its distal end (see FIG. 10). In the illustrative embodiment described herein, the medial end surface 402 has a width of at least 3 millimeters, although narrower medial end surface 402 widths may exist in other embodiments depending on, for example, the particular size of the tibial augment 104 and/or the size of the tibial tray 102.

When both tibial augments 104 are secured to the tibial tray 102, as depicted in FIGS. 3 and 15-17, there is formed a gap 1500 between the opposing medial end surfaces 402 of the tibial augments 104. The width of the gap 1500 may vary between embodiments, as further explained below.

It should be appreciated that the width of the medial end surface 402 is narrow relative to the width (that is, the distance between the interior side surface 123 and the exterior side surface 124) of other portions of the tibial augment 104. If the exterior side surface 124 were angled at its anterior-most point 406 to form an acute angle relative to the top proximal surface 124, the width of the bottom distal surface 122 near the anterior-most point 406, and the width of the distal portion of the medial end surface 402, would become even narrower. It should be appreciated that as this area becomes more narrow, the likelihood that such a narrow feature of the tibial augment would pose risks to the surgical procedure increase. For example, the narrow area could become sharp enough to damage soft tissue in the area of the implantation or could potentially break off during implantation or post-surgery. Conversely, the illustrative embodiment described herein, in which the side surface section 404 forms a substantial right angle at the anterior-most point 406 with the top proximal surface 120 and the bottom distal surface 122 of the exterior side surface 124 and in which the medial end surface 402 has a constant width of at least 3 mm, may avoid such problems caused by an overly narrow anterior surface and allows for greater ease of manufacturing.

Figure 13:
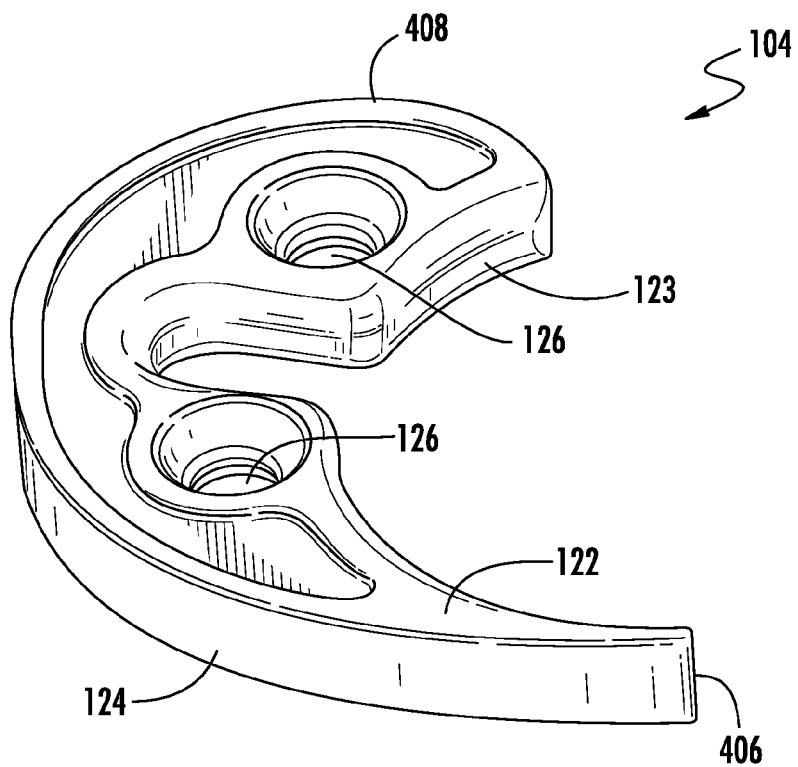
FIG. 13 is a perspective view of another embodiment of a tibial augment of the tibial orthopaedic prosthesis assembly of FIG. 1.
Figure 14:
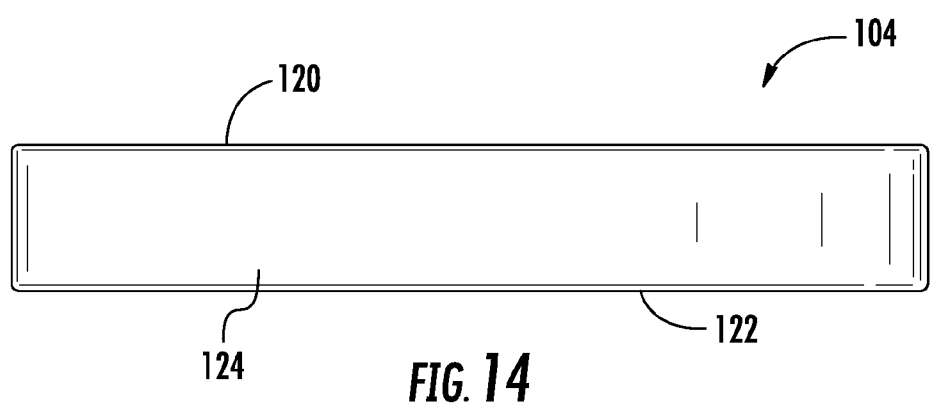
FIG. 14 is a front elevation view of the tibial augment of FIG. 13.

Referring now to FIGS. 13 and 14, an alternative embodiment of a tibial augment 104 is illustrated. In the embodiment illustrated in FIGS. 13 and 14, the tibial augment 104 is significantly thinner from its top proximal surface 120 to its bottom distal surface 122 as compared to the illustrative embodiment heretofore described. In embodiments such as that depicted in FIGS. 13 and 14, in which the tibial augment 104 is relatively thin, the side surface section 404 may form a right angle relative to the top proximal surface 120 throughout the length of the exterior side surface 124. Thus, FIGS. 13 and 14 depict the entire exterior side surface 124 extending orthogonally from both the top proximal surface 120 and the bottom distal surface 122.

Figure 15:
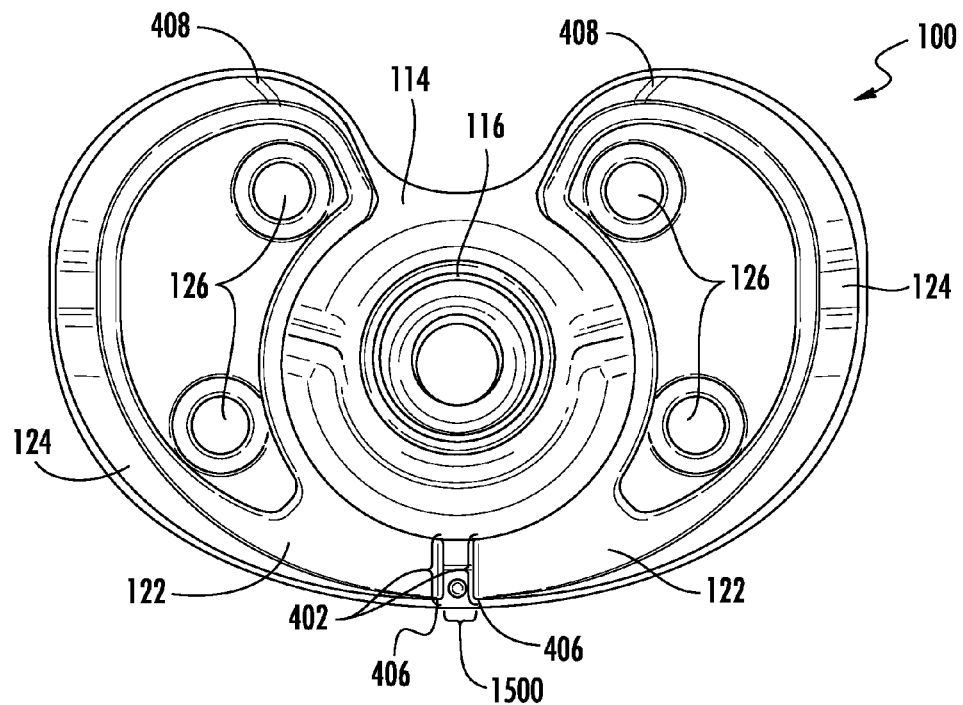
FIGS. 15-17 are bottom elevation views of the tibial orthopaedic prosthesis assembly of FIG. 3 showing tibial augments of varying sizes and with varying spacing between the medial end surfaces of the tibial augments.
Figure 16:
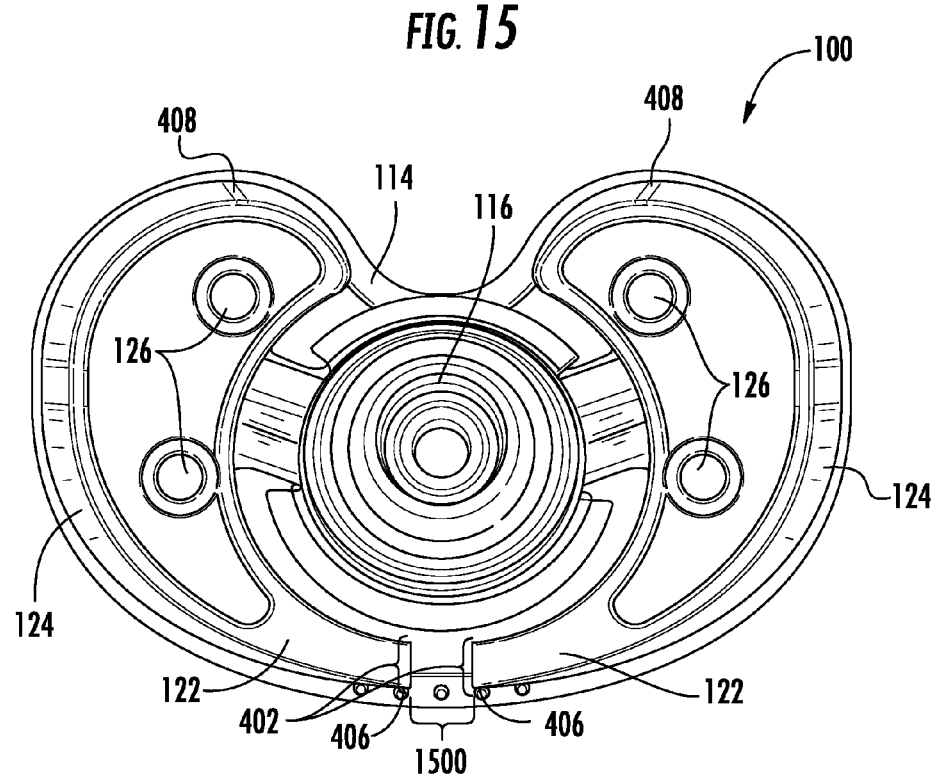
Figure 17:
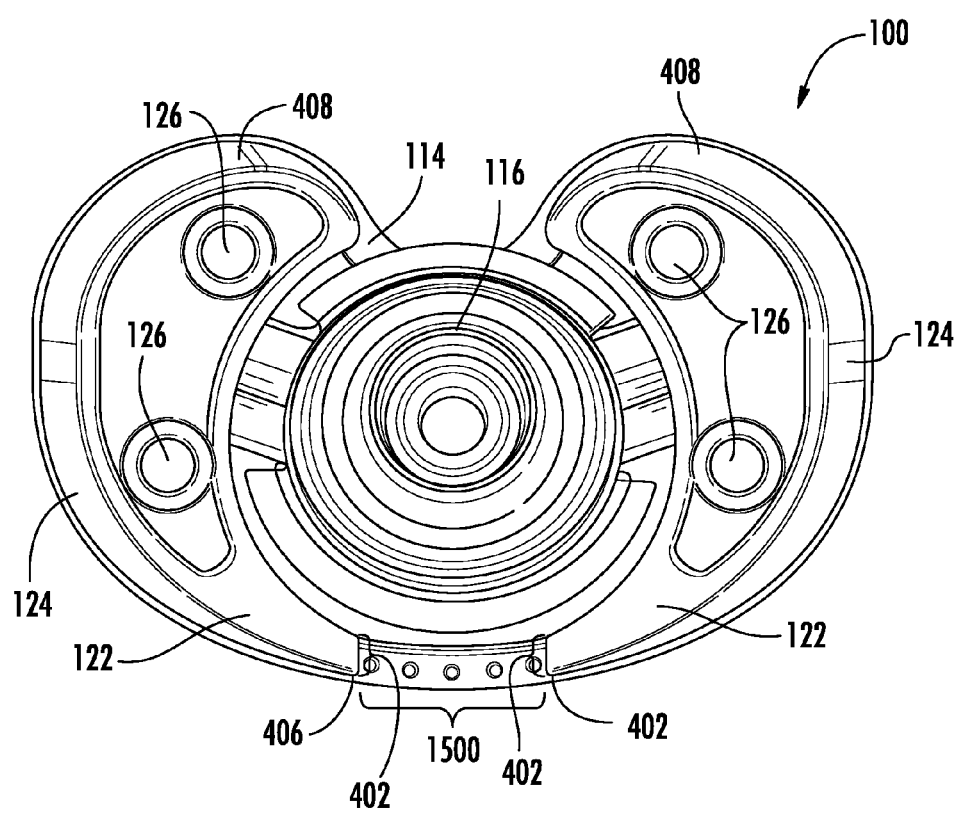

Referring now to FIGS. 15-17, the tibial orthopaedic prosthesis assemblies 100 having different sizes of tibial augments 104 are shown. The size of the tibial augments 104 used for a given surgical procedure may be dependent upon the size of the patient's tibial bony anatomy and/or the size the tibial tray 102 used in the orthopaedic surgical procedure. It should be appreciated that tibial augments 104 are intended to be suitable for use with patients having tibial bony anatomy of many different sizes. Tibial augments 104 are thus available in a variety of sizes. Likewise, the tibial tray 102 may be provided in various different sizes to fit the needs of a given patient's anatomy.

FIGS. 15-17 also illustrate variations in the width of the gap 1500 between the medial end surfaces 402 of the tibial augments 104 when secured to the tibial tray 102. In some embodiments, as in FIG. 17, it is preferred to leave a larger gap 1500 between the medial end surfaces 402 in order to maintain a desired thickness of the medial end surfaces 402. For example, depending on the size of the tibial augments 104, a gap of at least 2 millimeters between the opposing medial end surfaces 402 may be maintained. Alternatively, in other embodiments using tibial augments 104 of different sizes, a gap of at least 5 millimeters between the opposing medial end surfaces 402 may be maintained. Maintaining the gap 1500 at a particular width ensures the width of the medial end surfaces 402 does not become too narrow. As described above, an overly narrow medial end surface 402 may create a higher risk that the tibial augment 104 may break, may hinder fixation to the patient's tibia, and/or may create manufacturing difficulties. For example, if the anterior portion of the tibial augments 104 depicted in FIG. 17 extended further medially, the medial end surfaces 402 as well as the top proximal surfaces 120 and bottom distal surfaces 122 near the medial end surfaces 402 would become overly narrow.

In the illustrative embodiments described herein, the thickness of the medial end surfaces 402 is at least 3 mm. However, it is contemplated that tibial augments 104 with narrower end surfaces 402 may also be used in some embodiments. In addition to concerns over the width of the anterior portion of the tibial augments 104, variations in the gap 1500 may also be appropriate to conform to the patient's specific anatomy.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

What is claimed is:

1. A tibial augment configured to be secured to an implantable prosthetic tibial tray, the tibial augment comprising:
- a top proximal surface that abuts a bottom surface of the tibial tray when the tibial augment is secured to the tibial tray;
- a bottom distal surface opposite the top proximal surface;
- an exterior side surface that extends from the top proximal surface to the bottom distal surface, the exterior side surface including a side surface section extending from an anterior-most point of the exterior side surface to a posterior-most point of the exterior side surface, wherein the side surface section defines (i) a first interior angle relative to the top proximal surface at the anterior-most point of the exterior side surface and (ii) a second interior angle relative to the top proximal surface at the posterior-most point of the exterior side surface that is different from the first interior angle;
- an interior side surface positioned opposite the exterior side surface, wherein the interior side surface defines a third interior angle with the top proximal surface that is a right angle; and
- a medial end surface extending from the top proximal surface to the bottom distal surface and from the exterior side surface to the interior side surface of the tibial augment at the anterior-most point of the exterior surface.

2. The tibial augment of claim 1, wherein the second interior angle is less than the first interior angle.

3. The tibial augment of claim 1, wherein the second interior angle is an acute angle.

4. The tibial augment of claim 1, wherein the first interior angle is a right angle.

5. The tibial augment of claim 1, wherein the side surface section defines a right angle relative to the top proximal surface at the anterior-most point of the exterior side surface and an acute interior angle relative to the top proximal surface at the posterior-most point of the exterior side surface.

6. The tibial augment of claim 1, wherein the side surface section defines a third interior angle relative to the bottom distal surface at the anterior-most point of the exterior side surface, the third interior angle being substantially equal to the first interior angle.

7. The tibial augment of claim 1, wherein the side surface section defines a third interior angle relative to the bottom distal surface at the posterior-most point of the exterior side surface, wherein the third interior angle is an obtuse angle.

8. The tibial augment of claim 1, wherein the side surface section has a non-constant angulation relative to the top proximal surface as the side surface section extends from the anterior-most point of the exterior side surface to the posterior-most point of the exterior side surface.

9. The tibial augment of claim 1, wherein the side surface section defines a third interior angle relative to the top proximal surface at a mid-point between the anterior-most point and the posterior-most point of the exterior side surface, wherein the third interior angle is an acute angle.

10. The tibial augment of claim 9, wherein the third interior angle is different from each of the first interior angle and the second interior angle.

11. The tibial augment of claim 1, wherein the top proximal surface has a surface area that is substantially greater than a surface area of the bottom distal surface.

12. The tibial augment of claim 1, wherein the width of the medial end surface is at least 3 millimeters.

13. The tibial augment of claim 1, further comprising an interior surface defining a mounting aperture that extends through the tibial augment and has a first opening defined in the top proximal surface and a second opening defined in the bottom distal surface.

14. The tibial augment of claim 1, wherein the bottom distal surface comprises a recess defined therein to receive a bracket of the tibial tray when the tibial augment is secured to the tibial tray.

15. An implantable orthopedic knee prosthesis comprising:
- a tibial tray having a platform and a stem extending downwardly from a bottom surface of the platform, the platform including a top surface, opposite the bottom surface, to receive a tibial bearing;
- a medial tibial augment secured to a medial side of the bottom surface of the platform, the medial tibial augment including (i) a first top surface that abuts the bottom surface of the platform, (ii) a first bottom surface opposite the first top surface, (iii) a first exterior side surface extending from the first top surface to the first bottom surface, wherein the first exterior side surface includes a first side section that is tapered defining a first plane that is non-perpendicular to the first top surface and the first bottom surface, (iv) a first interior side surface extending from the first top surface to the first bottom surface, wherein the first interior side is perpendicular to the first top surface and the first bottom surface, and (v) a first medial end surface extending from the first top surface to the first bottom surface and from the first exterior side surface to the first interior side surface of the tibial augment, wherein the first medial end surface has a constant width; and
- a lateral tibial augment secured to a lateral side of the bottom surface of the platform, the lateral tibial augment including (i) a second top surface that abuts the bottom surface of the platform, (ii) a second bottom surface opposite the second top surface, (iii) a second exterior side surface extending from the second top surface to the second bottom surface, wherein the second exterior side surface includes a second side section that is tapered defining a second plane that is non-perpendicular to the second top surface and the second bottom surface, (iv) a second interior side surface extending from the second top surface to the second bottom surface, wherein the second interior side is perpendicular to the second top surface and the second bottom surface, and (v) a second medial end surface extending from the second top surface to the second bottom surface and from the second exterior side surface to the second interior side surface of the tibial augment, wherein the second medial end surface has a constant width,
- wherein the first medial end surface and the second medial end surface oppose each other toward an anterior side of the platform and are spaced apart from each other.

16. The implantable orthopedic knee prosthesis of claim 15, wherein the first medial end surface and the second medial end surface are spaced apart by at least 2 millimeters.

17. The implantable orthopedic knee prosthesis of claim 16, wherein the first medial end surface and the second medial end surface are spaced apart by at least 5 millimeters.

18. The implantable orthopedic knee prosthesis of claim 15, wherein:
- the first top surface of the medial tibial augment has a surface area that is greater than the surface area of the first bottom surface of the medial tibial augment, and
- the second top surface of the lateral tibial augment has a surface area that is greater than the surface area of the second bottom surface of the lateral tibial augment.

* * * * *